United States Patent [19]
McBrayer et al.

[11] Patent Number: 6,090,108
[45] Date of Patent: Jul. 18, 2000

[54] BIPOLAR ENDOSCOPIC SURGICAL SCISSOR BLADES AND INSTRUMENT INCORPORATING THE SAME

[75] Inventors: Michael Sean McBrayer, Miami; F. Anthony Headley, Jr., Pembroke Pines; Charles R. Slater, Fort Lauderdale, all of Fla.

[73] Assignee: Symbiosis Corporation, Miami, Fla.

[21] Appl. No.: 08/896,074

[22] Filed: Jul. 17, 1997

Related U.S. Application Data

[63] Continuation of application No. 08/495,224, Jun. 27, 1995, which is a continuation-in-part of application No. 08/429,596, Apr. 27, 1995, Pat. No. 5,779,701.

[51] Int. Cl.$^7$ .................................................. A61B 17/39
[52] U.S. Cl. .............................................. 606/46; 606/48
[58] Field of Search ................................ 606/174, 175, 606/45, 46, 48

[56] References Cited

U.S. PATENT DOCUMENTS

| | | |
|---|---|---|
| 636,473 | 11/1899 | Thuillier . |
| 2,579,773 | 12/1951 | Williams ................................... 30/350 |
| 3,651,811 | 3/1972 | Hilderbrandt . |
| 4,422,240 | 12/1983 | Wallace et al. ........................... 30/254 |
| 4,592,141 | 6/1986 | Levine ...................................... 30/138 |
| 4,709,480 | 12/1987 | Takigawa et al. ........................ 30/254 |
| 5,324,289 | 6/1994 | Eggers . |
| 5,330,471 | 7/1994 | Eggers . |
| 5,484,436 | 1/1996 | Eggers et al. ............................. 606/48 |

*Primary Examiner*—Michael H. Thaler
*Attorney, Agent, or Firm*—Finnegan, Henderson, Farabow, Garrett & Dunner, L.L.P.

[57] ABSTRACT

A bipolar endoscopic scissors is provided with scissor blades where at least one scissor blade is coated with an electrically non-conductive ceramic from its cutting edge along at least a contiguous portion of its shearing surface. The coated blade is provided with a cutting edge having an obtuse included angle which is preferably between approximately 95°–140°, and more preferably between 110° and 120°. The blades according to the invention may be configured in several different ways with regard to the number of layers and types of material used, the extent of the ceramic coating, and whether one or both blades are configured in an identical manner. The blades according to the invention having cutting edges defined by obtuse angles cut well and provide a good cutting feel to the practitioner while preventing the ceramic coating from chipping at the cutting edge.

54 Claims, 4 Drawing Sheets

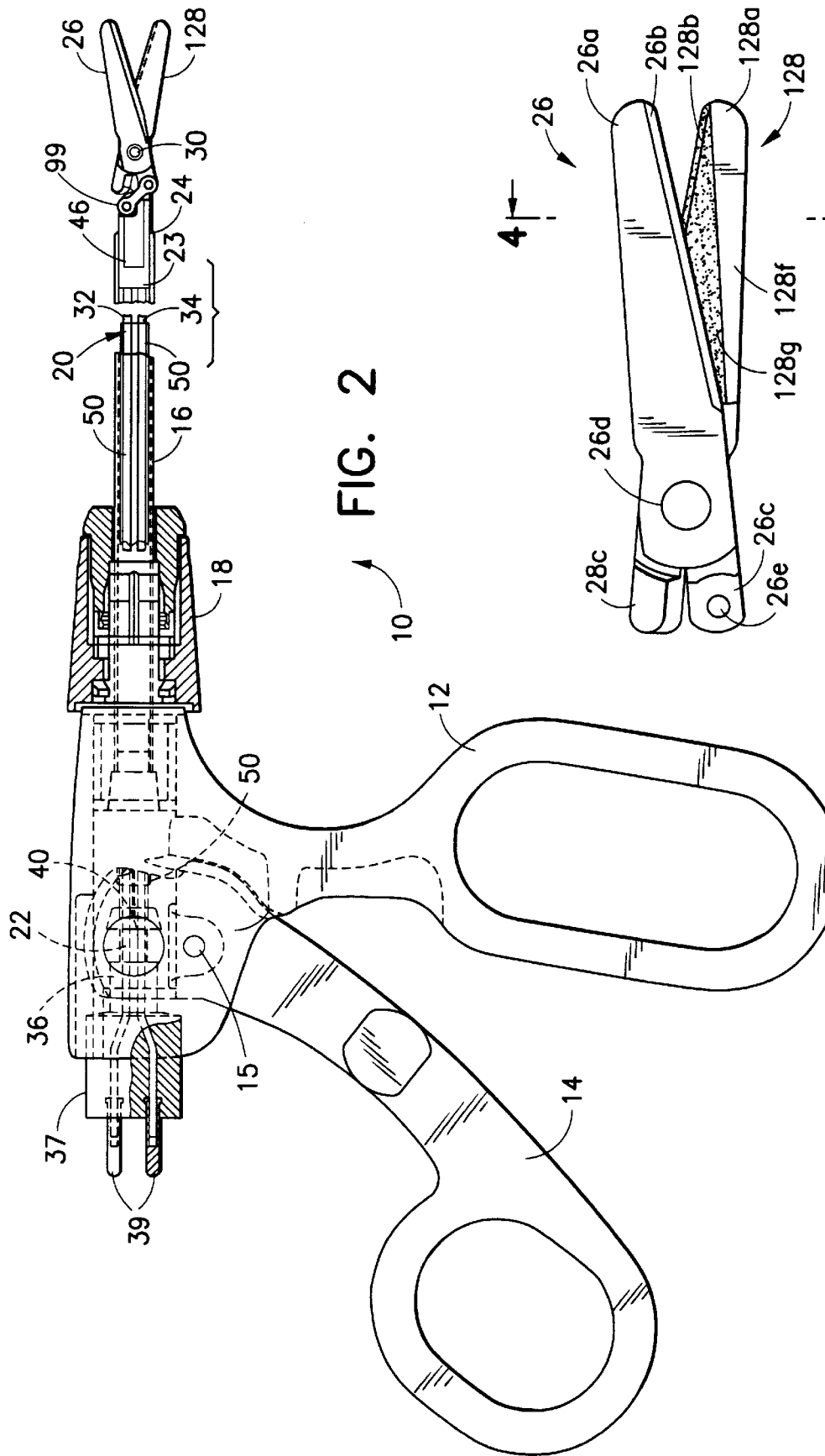

BIPOLAR ENDOSCOPIC SURGICAL SCISSOR BLADES AND INSTRUMENT INCORPORATING THE SAME

This application is a continuation of application Ser. No. 08/495,224, filed Jun. 27, 1995, which is a continuation-in-part of application Ser. No. 08/429,596, filed Apr. 27, 1995, now U.S. Pat. No. 5,779,701.

This application is a continuation in part of Ser. No. 08/429,596 filed Apr. 27, 1995, the complete disclosure of which is hereby incorporated by reference herein. This application is also related to U.S. Ser. No. 08/284,793 filed Aug. 2, 1994, now U.S. Pat. No. 5,569,243, U.S. Ser. No. 08/354,992 filed Dec. 13, 1994, and U.S. Ser. No. 08/377,156 filed Jan. 24, 1995, now abandoned the complete disclosures of which are hereby incorporated by reference herein.

BACKGROUND OF THE INVENTION

1. Field of the Invention

The present invention relates generally to endoscopic surgical instruments. More particularly, the invention relates to an endoscopic surgical instrument having end effectors made out of a combination of conductive and non-conductive materials. The invention has particular use with respect to bipolar endoscopic cautery. For purposes herein, the term "endoscopic instruments" is to be understood in its broadest sense and to include laparoscopic, arthroscopic, and neurological instruments, as well as instruments which are inserted through an endoscope, although it is not limited thereto.

2. State of the Art

Endoscopic surgery is widely practiced throughout the world today and its acceptance is growing rapidly. In general, endoscopic/laparoscopic surgery involves one or more incisions made by trocars where trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the optical instrument in place in the trocar tube.

Various types of endoscopic surgical instruments are known in the art. One type of instrument generally comprises a slender tube containing a push rod which is axially movable within the tube by means of a handle or trigger-like actuating means. An end effector is provided at the distal end of the tube and is coupled to the push rod by means of a clevis so that axial movement of the push rod is translated to rotational or pivotal movement of the end effector. End effectors may take the form of scissors, grippers, cutting jaws, forceps, and the like. Because of their very small size and the requirements of strength and/or sharpness, end effectors are difficult to manufacture and are typically formed of forged stainless steel, or are cast from bronze or from a superalloy.

Modern endoscopic procedures often involve the use of electrocautery, as the control of bleeding by coagulation during surgery is critical both in terms of limiting loss of blood and in permitting a clear viewing of the surgical site. As used herein, cautery, electrocautery, and coagulation are used interchangeably. Several types of electrocautery devices for use in endoscopic surgery are described in the prior art. Monopolar electrosurgical instruments employ the instrument as an electrode, with a large electrode plate beneath and in contact with the patient serving as the second electrode. High frequency voltage spikes are passed through the instrument to the electrode (i.e., end effector) of the endoscopic instrument to cause an arcing between the instrument and the proximate tissue of the patient. The current thereby generated continues through the patient to the large electrode plate beneath the patient. Monopolar cautery has the disadvantage that the current flows completely through the patient. Because control of the current path through the body is not possible, damage can occur to tissue both near and at some distance from the surgical site. In addition, it has been observed that monopolar cautery can result in excessive tissue damage due to the arcing between the end effector and the tissue.

In order to overcome the problems associated with monopolar cautery instruments, bipolar instruments have been introduced. In bipolar electrosurgical instruments, two electrodes which are closely spaced together are utilized to contact the tissue. Typically, one end effector acts as the first electrode, and the other end effector acts as the second electrode, with the end effectors being electrically isolated from each other and each having a separate current path back through to the handle of the instrument. Thus, in a bipolar instrument, the current flow is from one end effector electrode, through the tissue to be cauterized, to the other end effector electrode.

Various endoscopic instruments with cautery capability are known in the art. Several hemostatic bipolar electrosurgical scissors have also been described. U.S. Pat. No. 3,651,811 to Hildebrandt describes a bipolar electrosurgical scissors having opposing cutting blades forming active electrodes. The described scissors enables a surgeon to sequentially coagulate the blood vessels contained in the tissue and then to mechanically sever the tissue with the scissor blades. In particular, with the described bipolar electrosurgical scissors, the surgeon must first grasp the tissue with the scissor blades, energize the electrodes to cause hemostasis, de-energize the electrodes, and then close the scissor blades to sever the tissue mechanically. The scissors are then repositioned for another cut accomplished in the same manner. With the bipolar electrosurgical scissors of Hildebrandt, the surgeon cannot maintain the electrodes in a continuously energized state because the power supply would be shorted out and/or the blades damaged if the blades are permitted to contact each other while energized.

The disadvantages of the bipolar scissors of Hildebrandt are overcome by the disclosure in U.S. Pat. Nos. 5,324,289 and 5,330,471 to Eggers. In its preferred embodiment, the bipolar electrosurgical scissors of Eggers comprise a pair of metal scissor blades which are provided with an electrically insulating material interposed between the shearing surfaces of the blades so that when the scissor blades are closed, the metal of one blade never touches the metal of the other blade; i.e., the insulating material provides the cutting edge and the shearing surface. With the arrangement provided by Eggers, a cautery current will pass from the top back edge of the bottom metal blade through the tissue which is to be cut and to the bottom back edge of the top metal blade directly in advance of the cutting action. As the scissors are gradually closed, the hemostasis preferentially occurs at a location just in advance of the cutting point which itself moves distally along the insulated cutting edges of the blades in order to sever the hemostatically heated tissue. With this arrangement, the scissors may be maintained in a continuously energized state while performing the cutting. The Eggers patent describes various alternative embodiments of the bipolar scissors, including the use of metal blades with only one blade being insulated on its shearing surface, and the use of insulating blades with back surfaces coated with metal.

The disadvantage of scissor blades which have non-conductive cutting edges and shearing surfaces is that they are difficult to operate. The non-conductive surfaces are relatively non-lubricous and do not have the smooth operation and feel of a metal on metal cutting/shearing action. Parent application Ser. No. 08/429,596 discloses scissor blades comprised of an electrically conductive electrode, an electrically insulating material, and a coating of titanium dioxide, chromium dioxide, or zirconium dioxide, where the coating provides a lubricious surface which simulates a metal on metal feel. In one embodiment, the electrode layer is a metal blade which is typically constructed from stainless steel, while the insulating layer is an alumina ceramic which is deposited, bonded, or otherwise fixed on the metal blade, and a titanium dioxide coating is deposited, bonded, or otherwise fixed onto the ceramic and provides the cutting edge and shearing surface. In another embodiment, the electrode layer of the scissor blades is a metal blade, and the titanium dioxide is mixed with the alumina ceramic and then applied directly to the conductive electrode. In this preferred embodiment, the ratio by weight of alumina ceramic to titanium dioxide is 87/13, although the ratio can range from 75/25 to 95/5 and still provide the desired insulation and lubricity. In a third embodiment of the invention, the insulating layer is a ceramic support, with the electrode layer and the titanium dioxide shearing surface layer being deposited, bonded, or otherwise fixed to opposite sides of the ceramic support. In all embodiments, since the coated cutting edges and preferably at least a portion of the shearing surfaces are insulated from the electrodes, no short circuit can form between the electrodes even though the cutting edge and shearing surface of each scissor blade are in contact with the cutting edge and shearing surface of the other scissor blade.

In the prior art, as well as in the parent application hereto, a cross sectional profile of an endoscopic scissor blade generally defines an included angle of between 60–90° at the cutting edge. This may be seen in the prior art Figures of 1 and 1a where the blades 26, 28 have an included angle α of approximately 70° at their cutting edges 26b, 28b. It is generally believed in the art that the cutting edge of a surgical scissor blade, and in particular an endosurgical scissor blade, must be defined by an angle of no more than 90° in order to achieve effective cutting.

U.S. Pat. No. 4,709,480 to Takigawa et al. disclosed a scissors for use in horticulture and for industrial purposes. Prior art FIG. 1b shows a cross section of the scissors which has one metallic cutting blade 11 and one ceramic cutting blade 12. Takigawa et al. teaches that if the cutting edge of a ceramic cutting blade is defined by an acute included angle, the ceramic is likely to be damaged. The inventors herein have confirmed that this is also true in the case of endoscopic scissors. According to Takigawa et al., the damage to the ceramic blade is most likely to be caused by the blades interfering with each other as the bow in the scissor blade causes their respective cutting edges to press against each other at a single moving point of contact as the blades are closed. The solution proposed by Takigawa et al. is to locate the cutting edge of the ceramic blade away from the shearing surface so that it never touches the cutting edge of the metallic blade. Thus, the cutting edge of the ceramic blade disclosed by Takigawa et al., as shown in prior art FIG. 1b, is defined by an adjacent side 16 which forms an obtuse angle $\theta_2$ with the shearing surface 15 and a beveled side 17. While Takigawa et al. does not specifically disclose what angle is formed by the adjacent side 16 and the beveled side 17 (i.e. the included angle of the cutting edge), it appears to be close to 90°. The scissors proposed by Takigawa et al. may have utility in horticulture and in some industrial applications. However, they are unsuitable for surgical procedures. As those skilled in the art will appreciate from prior art FIG. 1b, when the scissors are used to cut article "c", the cutting edge of the metallic blade 11 will attempt to sever the article along a virtual plane A-B. Since the cutting edge of the ceramic blade 12 is not located in the plane A-B, it will pull the article c up and away from the plane A-B. Thus, depending on the nature of the article c, it may be torn apart rather than cut. Scissors of this design would certainly tear, rather than sever, human tissue.

SUMMARY OF THE INVENTION

It is therefore an object of the invention to provide an endoscopic scissor blade which includes a ceramic coating which is resistant to chipping.

It is another object of the invention to provide a pair of scissor blades for a bipolar cauterizing surgical scissors which have shearing surfaces that are insulated from cautery surfaces.

It is also an object of the invention to provide a pair of scissor blades for a bipolar cauterizing surgical scissors which provide the smooth operation and feel of a metal on metal cutting/shearing action, and which cut well.

In accord with the objects of the invention, a pair of bipolar endoscopic scissor blades is provided in which at least one scissor blade is coated with an electrically non-conductive ceramic from its cutting edge along at least a contiguous portion of its shearing surface, with the cutting edge of the coated blade defining an obtuse angle. The obtuse angle of the cutting edge is preferably more than 95° and less than 140°, and more preferably between approximately 110° and 120°.

The blades according to the invention may be configured in several different ways with regard to the number of layers and types of material used, the extent of the ceramic coating, and whether one or both blades are configured in an identical manner. In a first embodiment, a scissor blade having a partial ceramic coating is used in conjunction with an uncoated metallic scissor blade having an acute angle cutting edge. In a second embodiment of the invention, two substantially identically configured ceramic coated blades are shown, both having obtuse angle cutting edges. Other embodiments of the invention include blades having fully coated shearing surfaces and blades which are laminates of several different materials. It has been discovered by the inventors herein that the blades according to the invention having cutting edges defined by obtuse angles cut well and provide a good cutting feel to the practitioner. As the angle of the cutting edge is increased above 90°, the integrity of the ceramic at the cutting edge is enhanced. Clearly, if the angle is too large, no cutting will be effected. It has been discovered by the inventors herein that an angle approximately 95–140° works well and that a presently preferred angle is between approximately 110° and 120°.

Additional objects and advantages of the invention will become apparent to those skilled in the art upon reference to the detailed description taken in conjunction with the provided figures.

BRIEF DESCRIPTION OF THE DRAWINGS

FIG. 2 is a broken side elevation view in partial section of an endoscopic bipolar scissors instrument;

FIG. 3 is an enlarged side elevation view of a pair of scissor blades incorporating a ceramic coating on one of the blades;

DETAILED DESCRIPTION OF THE PREFERRED EMBODIMENTS

Figure 1:
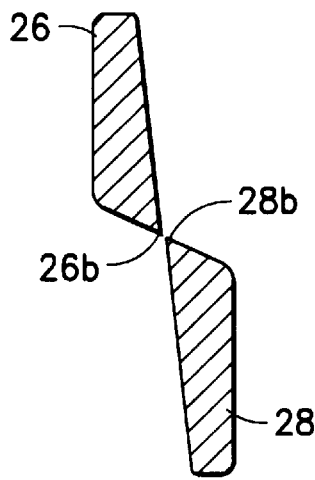
FIG. 1 is an enlarged cross sectional view of prior art endoscopic scissor blades.
Figure 1A:
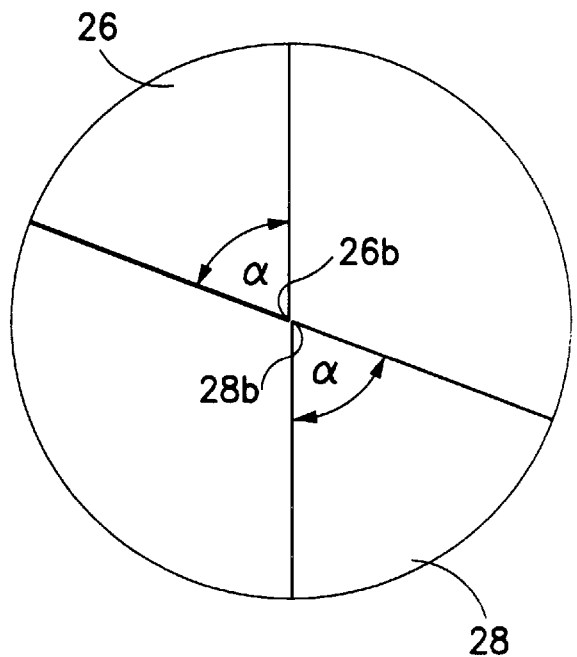
FIG. 1a is a further enlarged portion of FIG. 1 showing the point of contact and the included angles of the cutting edges of the prior art scissor blades.
Figure 1B:
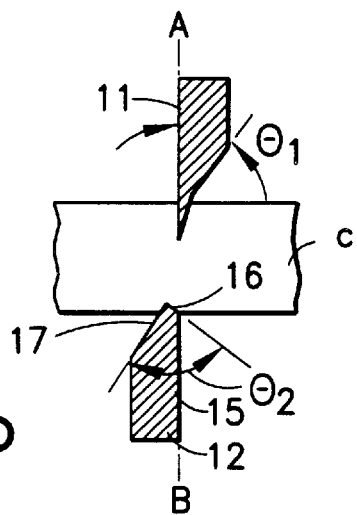
FIG. 1b is a view similar to FIG. 1 of prior art horticultural scissor blades.

FIG. 2 shows the endoscopic bipolar cautery scissors instrument 10, utilized in the parent application and the related applications incorporated by reference herein above in which the end effectors of the present invention find use. The endoscopic bipolar scissors instrument 10 includes a proximal handle 12 with a manual lever actuator 14 pivotally coupled to the handle by a pivot pin 15. A hollow stainless steel tube 16 is rotatably coupled to the handle 12 and is preferably rotatable about its longitudinal axis relative to the handle 12 through the use of a ferrule 18 such as described in detail in previously incorporated copending application Ser. No. 08/284,793. A push rod assembly 20 extends through the hollow tube 16 and is coupled at its proximal end 22 to the manual lever actuator 14 as described in more detail in copending application Ser. No. 08/284,793. The distal end of the tube 16 has an integral clevis 24 within which a pair of scissor blades 26, 128 are mounted on an axle screw 30. The distal end 23 of the push rod assembly 20 is coupled to the scissor blades 26, 128 so that reciprocal movement of the push rod assembly 20 relative to the tube 16 opens and closes the scissor blades 26, 128. It will be appreciated that the reciprocal movement of the push rod assembly 20 relative to the tube 16 is effected by movement of the manual lever actuator 14 relative to the handle 12.

The presently preferred embodiment of the push rod assembly 20 includes a pair of stainless steel rods 32, 34 which are molded into a proximal collar 36 and captured in a distal collar 46. The proximal collar has a radial groove 40 in its distal portion and an increased diameter proximal portion 37 which carries a pair of electrical coupling pins 39 which are electrically coupled to the rods 32, 34. As shown, the pins 39 are spaced farther apart from each other than the rods 32, 34 so as to accommodate a standard cautery connector. While the proximal collar shown has a male connector, a female connector may be used instead. The rods 32, 34 are covered with an insulating double lumen polypropylene tube 50 along substantially their entire length between the proximal and distal collars 36, 46. The double lumen tube 50 may be discontinuous at a point inside the tube 16 to provide a rubber air flow seal (not shown) on the rods 32, 34. According to a presently preferred embodiment, the distal collar 46 is made from a single ceramic piece. The electrically conductive rods 32, 34 exit the distal collar 46 through opposite sides at substantially right angles. The distal ends of the rods 32, 34 are mechanically and electrically coupled to the respective blades 26, 128 by respective electrically conductive links 99.

As shown in FIG. 3 the first scissor blade 26 has a distal portion 26a, a lower proximal tang 26c, and a mounting hole 26d therebetween. A connecting lug 26e extends orthogonally outward from the surface of the tang 26c in a first direction. The distal portion 26a includes a lower cutting edge 26b and an inner surface 26f (also called the shearing surface). The opposed second scissor blade 128 is configured similarly to the first scissor blade and has a distal portion 128a, an upper proximal tang 128c, and a mounting hole 128d therebetween. A connecting lug (not shown) extends orthogonally from the surface of the tang 128c in a second direction which is opposite to the first direction mentioned above. The distal portion 128a includes an upper cutting edge 128b (defining an obtuse angle as discussed below) and an inner surface 128f. According to the parent application and the present invention, at least one of the scissor blades 26, 128 (in this case blade 128) is coated with an electrically non-conductive ceramic 128g from its cutting edge 128b along at least a contiguous portion of its shearing surface 128f.

Figure 4:
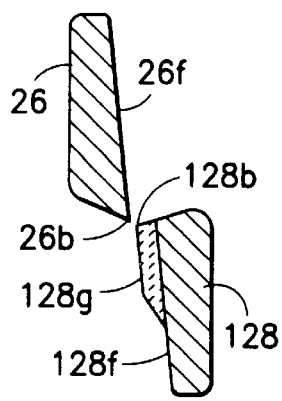
FIG. 4 is an enlarged cross sectional view taken at 4—4 of FIG. 3 and showing a first embodiment of the invention.
Figure 4A:
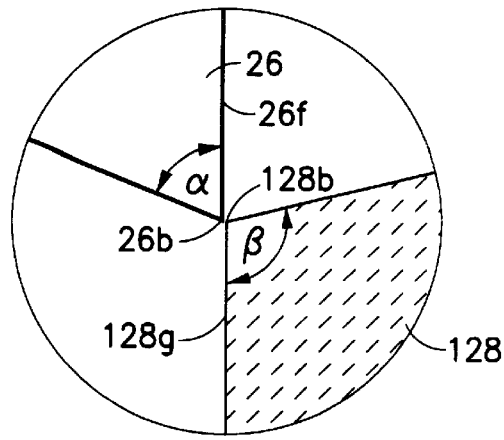
FIG. 4a is a view similar to FIG. 1a and showing the included angles of the blades of the first embodiment of the invention.

Turning now to FIGS. 4 and 4a, details of the cutting edges of a first embodiment of bipolar scissor blades according to the invention are seen. The conventional metal blade 26 has a shearing surface 26f and a cutting edge 26b which is defined by an included angle $\alpha$ of approximately 60°–90°. The scissor blade 128 has a shearing surface 128f which is partially coated with a ceramic material 128g adjacent to its cutting edge 128b. The cutting edge 128b of the blade 128 is defined by an obtuse angle $\beta$ which is preferably more than 95° and less than 140°, and more preferably between approximately 110° and 120°. When used in a bipolar endosurgical instrument such as the one shown in FIG. 1, the blades 26, 128 provide the smooth operation and feel of a metal on metal cutting/shearing action. The ceramic coating 128g on the blade 128 insures that the shearing surfaces 26f, 128f of the blades are electrically insulated from each other so that cautery current my be constantly supplied throughout a cutting procedure. The included obtuse angle of the cutting edge 128b of the blade 128 prevents the ceramic coating 128f from chipping at the cutting edge 128b. Despite the fact that the cutting edge of the coated blade 128 is defined by an obtuse angle, the scissors cut very well.

Figure 5:
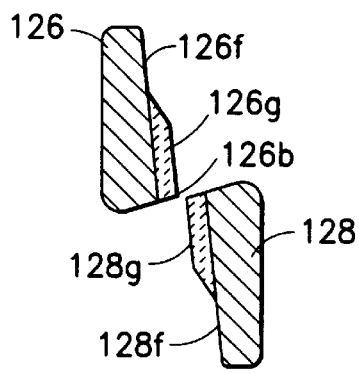
FIG. 5 is a view similar to FIG. 4 of a second embodiment of the invention.
Figure 5A:
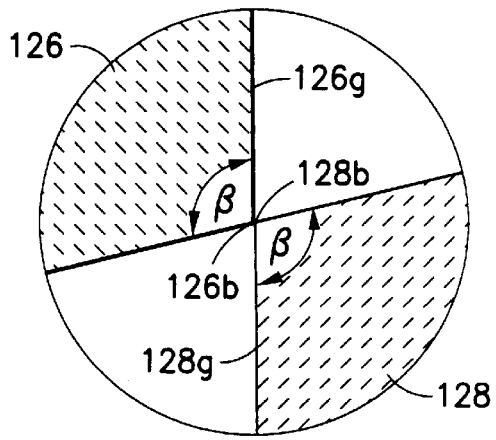
FIG. 5a is a view similar to FIG. 4a of the second embodiment of the invention.

According to a second embodiment of the invention shown in FIGS. 5 and 5a, a pair of bipolar scissor blades according to the invention includes two partially ceramic coated metal blades 126 and 128. In this embodiment, the blade 126 is configured substantially the same as the blade 128 described above. When used in a bipolar endosurgical instrument such as the one shown in FIG. 1, the blades 126, 128 provide the smooth operation and feel of a metal on metal cutting/shearing action. The ceramic coatings 126g, 128g on the blades 126, 128 insure that the shearing surfaces 126f, 128f of the blades are electrically insulated from each other so that cautery current my be constantly supplied throughout a cutting procedure. The included obtuse angles of the cutting edges 126b, 128b of the blades 126, 128 prevents the ceramic coatings 126f, 128f from chipping at the cutting edges 126b, 128b. Despite the fact that the cutting edges are defined by obtuse angles, the scissors cut very well.

Figure 6:
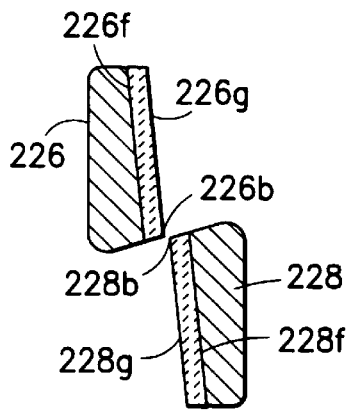
FIG. 6 is a view similar to FIG. 5 of a third embodiment of the invention.

According to a third embodiment of the invention shown in FIG. 6, a pair of bipolar scissor blades according to the invention includes metal blades 226 and 228. In this embodiment, both blades 226 and 228 have a shearing surface 226f, 228f which is substantially completely coated with a ceramic material 226g, 228g and a cutting edge 226b, 228b which is defined by an obtuse angle. When used in a bipolar endosurgical instrument such as the one shown in FIG. 1, the blades 226, 228 provide the smooth operation and feel of a metal on metal cutting/shearing action. The ceramic coatings 226g, 228g on the blades 226, 228 insure that the shearing surfaces 226f, 228f of the blades are electrically insulated from each other so that cautery current may be constantly supplied throughout a cutting procedure. The included obtuse angles of the cutting edges 226b, 228b of the blades 226, 228 prevents the ceramic coatings 226f, 228f from chipping at the cutting edges 226b, 228b. Despite the fact that the cutting edges are defined by obtuse angles, the scissors cut very well.

From the foregoing, it will be appreciated either of the scissor blades 128, 228 may be used with any of the blades 26, 126, 226. Moreover, although not shown, the non-coated blade 26 may be provided with a 90° or obtuse angle cutting edge if desired to impart symmetry to the scissor blades and/or to reduce the cost of manufacture by casting both blades in the same die.

Figure 7:
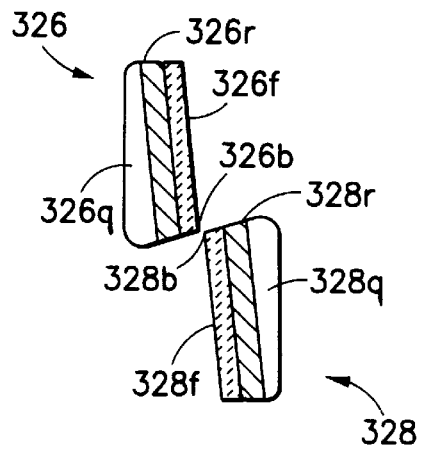
FIG. 7 is a view similar to FIG. 6 of a fourth embodiment of the invention.

As described in the parent application, bipolar scissor blades may be made of a laminate of several conductive and non-conductive materials. FIG. 7 shows an example of two scissor blades 326, 328 which are each composite laminates of conductive and non-conductive material. Typically, the shearing surface 326f, 328f of the blades will be a ceramic material in order to provide the metal-on-metal feel taught by the parent application. The middle portion 326r, 328r of the laminate may be either conductive or non-conductive and the outer portion 326q, 328q of the laminate may be either conductive or non-conductive provided that at least one of the middle portion and the outer portion is conductive. In accord with the invention, the blades having ceramic coated shearing surfaces are provided with cutting edges defined by an obtuse angle.

Figure 8A:
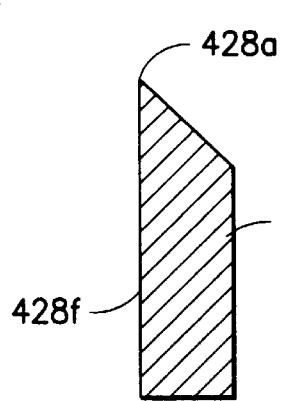
FIGS. 8a through 8c are enlarged sectional views illustrating a presently preferred method of making the scissor blades of the invention.
Figure 8B:
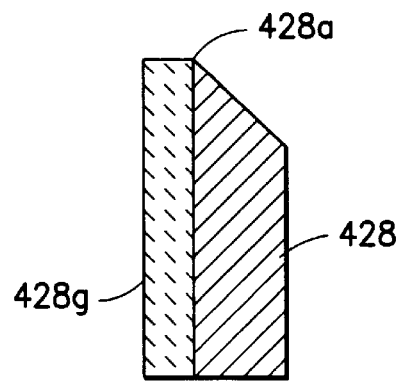
Figure 8C:
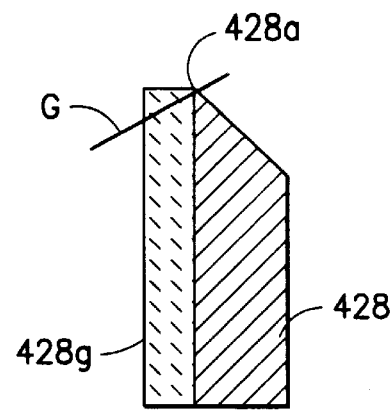
Figure 9:
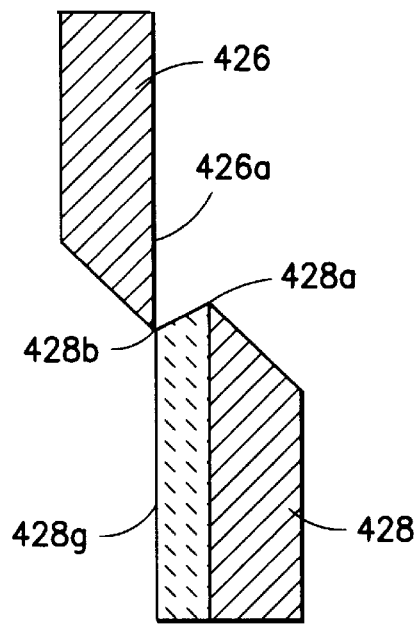
FIG. 9 is a view similar to FIG. 6 illustrating a presently preferred embodiment of the invention.

A presently preferred method of making the scissor blades according to the invention is illustrated in FIGS. 8a–8c and 9. A metallic scissor blade 428 having an acute angle cutting edge 428a, as shown in FIG. 8a, is obtained. A ceramic coating 428g is applied to the shearing surface 428f of the blade as shown in FIG. 8b. The blade 428 and the coating 428g are then ground along a line "G" as shown in FIG. 8c to form an obtuse angle cutting edge 428b as shown in FIG. 9. A second all-metal scissor blade 426 having an acute angle cutting edge 426a is also obtained, and the two scissor blades 426, 428 are arranged as shown in FIG. 9 so that cutting takes place at the point where there respective cutting edges 426a, 428b meet. The former cutting edge 428a of the ceramic coated blade is rendered sufficiently dull and is spaced far enough apart from the cutting edge 428b so that no cutting or tearing is effected by the former cutting edge 428a. If desired, to further insure that cutting occurs only at edges 426a and 428b, the metal edge 428a may be rounded in a further grinding step.

There have been described and illustrated herein several embodiments of bipolar endoscopic surgical scissor blades and an instrument incorporating them. While particular embodiments of the invention have been described, it is not intended that the invention be limited thereto, as it is intended that the invention be as broad in scope as the art will allow and that the specification be read likewise. Thus, while particular conductive and non-conductive materials have been disclosed, it will be appreciated that other materials could be utilized. Also, while blades of specific shape and dimension have been shown, it will be recognized that blades having different shapes and dimensions could be used with similar results obtained. While means for pivotally joining the blades has been shown as an axle screw with a nut, other pivotal joining means could be used. For example, a clevis with an integral axle pin, or a snap-in axle pin, or a riveted axle pin could all be used. While means for supplying each blade with a voltage has been shown as a bipolar push rod, it will be appreciated that other means such as a bipolar clevis and bipolar hollow tube could be used. Individual shielded electrical conductors within the hollow tube could also be used for this purpose. In addition, while the electrical coupling of the conductive portion of each blade has been shown as the proximal connecting lug which connects to a link, it will be appreciated that an electrical coupling could be made through a two piece bipolar clevis axle. Also, while the means for imparting scissor-like movement to the blades has been shown as a push rod, a pull wire or other reciprocating arrangement might be used as well. In addition, while the means for coupling the scissor blades to the push rod has been shown as an orthogonal lug, it will be understood that other means such as a connecting hole could be used while achieving substantially the same results. Moreover, while particular methods have been disclosed in reference to laminating conductive and non-conductive layers, it will be appreciated that other methods could be used as well. Also, it will be appreciated that provision of an obtuse angle cutting edge on a scissor blade having a ceramic coating on its shearing surface may be applied to many different types of scissor blades and the scissor blades described herein are to be considered exemplary rather than limiting. It will therefore be appreciated by those skilled in the art that yet other modifications could be made to the provided invention without deviating from its spirit and scope as so claimed.

What is claimed is:

1. A bipolar electrosurgical instrument, comprising:

a) a first blade member having an electrically conductive portion, a shearing surface and a cutting edge, b) a second blade member having an electrically conductive portion, a shearing surface and a cutting edge, said second blade member bearing a ceramic coating on at least part of its shearing surface, the cutting edge of said second blade member being defined by an obtuse included angle and lying in a first plane which is substantially coplanar with its shearing surface, said second blade member having no cutting edge lying outside said first plane, said second blade member having a second substantially planar surface lying in a second plane which intersects said first plane along said cutting edge, said second substantially planar surface including a substantially planar portion of said electrically conductive portion;

c) means for pivotally joining said first and second blade members together with their respective shearing surfaces facing one another;

d) means coupled to at least one of said first and second blade members for inparting a scissors-like movement relative to the other of said first and second blade members; and e) means for applying a voltage between the electrically conductive portions of said first and second blade member.

2. A bipolar electrosurgical instrument according to claim 1, wherein:
said first blade member has a cutting edge which is defined by an acute included angle.

3. A bipolar electrosurgical instrument according to claim 1, wherein:
said first blade member has a cutting edge which is defined by an obtuse included angle.

4. A bipolar electrosurgical instrument according to claim 3, wherein:
said first blade member has a ceramic coating on at least part of its shearing surface.

5. A bipolar electrosurgical instrument according to claim 4, wherein:
said second blade member has a ceramic coating on substantially all of its shearing surface and said first blade member has a ceramic coating on substantially all of its shearing surface.

6. A bipolar electrosurgical instrument according to claim 1, wherein:
said second blade member has a ceramic coating on substantially all of its shearing surface.

7. A bipolar electrosurgical instrument according to claim 6, wherein:
said obtuse included angle is between 110° and 120°.

8. A bipolar electrosurgical instrument according to claim 1, wherein:
said second blade member comprises a laminated assembly including an electrically conductive layer and an electrically non-conductive layer.

9. A bipolar electrosurgical instrument according to claim 8, wherein:
said first blade member comprises a laminated assembly including an electrically conductive layer and an electrically non-conductive layer.

10. A bipolar electrosurgical instrument according to claim 8, wherein:
said obtuse included angle is between 110° and 120°.

11. A bipolar electrosurgical instrument according to claim 1, wherein:
said obtuse included angle is at least as great as 95°.

12. A bipolar electrosurgical instrument according to claim 11, wherein:
said obtuse included angle is less than approximately 140°.

13. A bipolar electrosurgical instrument according to claim 12, wherein:
said obtuse included angle is between 110–120°.

14. An endoscopic scissor blade for use in a bipolar endoscopic instrument, said blade comprising:
a) an electrically conductive portion;
b) a shearing surface which is at least partially coated with ceramic; and
c) a cutting edge which is defined by an obtuse included angle and which lies in a plane which is substantially coplanar with said shearing surface,
said scissor blade having an inner face and an outer face, said cutting edge and said shearing surface lying on said inner face, an entirely blunt leading surface extending from said outer face to said cutting edge.

15. An endoscopic scissor blade according to claim 14, further comprising:
d) means for pivotally mounting said scissor blade; and
e) means for coupling said scissor blade to a means for imparting a pivotal movement to said scissor blade.

16. An endoscopic scissor blade according to claim 14, wherein:
said shearing surface is substantially entirely coated with ceramic.

17. An endoscopic scissor blade according to claim 14, wherein:
said obtuse included angle is at least as great as 95°.

18. An endoscopic scissor blade according to claim 17, wherein:
said obtuse included angle is less than 140°.

19. An endoscopic scissor blade according to claim 18, wherein:
said obtuse included angle is between 110° and 120°.

20. A bipolar electrosurgical instrument, comprising:
a) a first blade member having an electrically conductive portion, a shearing surface and a cutting edge,
b) a second blade member having an electrically conductive portion, a shearing surface, an electrically non-conductive material having an inner surface on the shearing surface and outer surface opposite the inner surface, a cutting edge, and a planar leading surface including a first planar surface portion of the electrically non-conductive material and a second planar surface portion of the electrically conductive portion which lies in the same plane as the first planar surface portion, the cutting edge being located at an intersection of the outer surface and the planar leading surface;
c) means for pivotally joining said first and second blade members together with their respective shearing surfaces facing one another;
d) means coupled to at least one of said first and second blade members for imparting a scissors-like movement relative to the other of said first and second blade members; and
e) means for applying a voltage to at least one of the electrically conductive portions of said first and second blade members.

21. A bipolar electrosurgical instrument according to claim 20, wherein:
voltage is applied to the electrically conductive portions of the first and second blade members.

22. A bipolar electrosurgical instrument according to claim 20, wherein:
the intersection of the outer surface and the planar leading surface forms an obtuse included angle.

23. A bipolar electrosurgical instrument according to claim 22, wherein:
said obtuse included angle is at least as great as 95°.

24. A bipolar electrosurgical instrument according to claim 23, wherein:
said obtuse included angle is less than approximately 140°.

25. A bipolar electrosurgical instrument according to claim 24, wherein:
said obtuse included angle is between 110° and 120°.

26. A bipolar electrosurgical instrument according to claim 20, wherein:
the non-conductive material is ceramic.

27. A bipolar electrosurgical instrument according to claim 20, wherein:

said first blade member has a cutting edge which is defined by an acute included angle.

28. A bipolar electrosurgical instrument according to claim 20, wherein:
said first blade member has a cutting edge which is defined by an obtuse included angle.

29. A bipolar electrosurgical instrument according to claim 28, wherein:
said first blade member has an electrically non-conductive material on at least part of its shearing surface.

30. A bipolar electrosurgical instrument according to claim 29, wherein:
said electrically non-conductive material of the second blade member is located on substantially all of its shearing surface and said first blade member has an electrically non-conductive material on substantially all of its shearing surface.

31. A bipolar electrosurgical instrument according to claim 20 wherein:
said electrically non-conductive material of the second blade member is located on substantially all of the second blade shearing surface.

32. A bipolar electrosurgical instrument according to claim 20, wherein:
said second blade member further comprises a laminated assembly including a second electrically non-conductive portion.

33. A bipolar electrosurgical instrument according to claim 20, wherein:
said first blade member further comprises a laminated assembly including two electrically non-conductive portions.

34. An endoscopic scissor blade for use in a bipolar endoscopic instrument, said blade comprising:
an electrically conductive portion having a shearing surface;
an electrically non-conductive material having an inner surface on the shearing surface and an outer surface opposite the inner surface; and
a planar leading surface including a first planar surface portion of the electrically non-conductive material and a second planar surface portion of the electrically conductive portion which lies in the same plane as the first planar surface portion, the planar leading surface intersecting the outer surface to define a cutting edge of the blade.

35. An endoscopic scissor blade according to claim 34, wherein:
the intersection of the outer surface and the planar leading surface forms an obtuse included angle.

36. An endoscopic scissor blade according to claim 35, wherein:
said obtuse included angle is at least as great as 95°.

37. An endoscopic scissor blade according to claim 36, wherein:
said obtuse included angle is less than 140°.

38. An endoscopic scissor blade according to claim 37, wherein:
said obtuse included angle is between 110° and 120°.

39. An endoscopic scissor blade according to claim 34 wherein:
the electrically non-conductive material is ceramic.

40. An endoscopic scissor blade according to claim 34 further comprising:
means for pivotally mounting said scissor blade; and
means for coupling said scissor blade to a means for imparting a pivotal movement to said scissor blade.

41. An endoscopic scissor blade according to claim 34, wherein:
said shearing surface is substantially entirely coated with non-conductive material.

42. A bipolar electrosurgical instrument, comprising:
a) a first blade member having an electrically conductive portion, a shearing surface and a cutting edge,
b) a second blade member having an electrically conductive portion, a shearing surface, an electrically non-conductive material having an inner surface on the shearing surface and outer surface opposite the inner surface, a cutting edge, and a planar leading surface including a first planar surface portion of the electrically non-conductive material and a second planar surface portion of the electrically conductive portion which lies in the same plane as the first planar surface portion, the cutting edge being located at an intersection of the outer surface and the planar leading surface;
c) a pivot assembly joining said first and second blade members together with their respective shearing surfaces facing one another;
d) an actuating assembly coupled to at least one of said first and second blade members for imparting a scissors-like movement relative to the other of said first and second blade members; and
e) a conducting assembly to conduct electric current to the electrically conductive portions of said first and second blade members to form a voltage between the electrically conductive portions of said first and second blade members.

43. A bipolar electrosurgical instrument according to claim 42, wherein:
the intersection of the outer surface and the planar leading surface forms an obtuse included angle.

44. A bipolar electrosurgical instrument according to claim 43, wherein:
said obtuse included angle is at least as great as 95°.

45. A bipolar electrosurgical instrument according to claim 44, wherein:
said obtuse included angle is less than approximately 140°.

46. A bipolar electrosurgical instrument according to claim 45, wherein:
said obtuse included angle is between 110° and 120°.

47. A bipolar electrosurgical instrument according to claim 42, wherein:
the non-conductive material is ceramic.

48. A bipolar electrosurgical instrument according to claim 42, wherein:
said first blade member has a cutting edge which is defined by an acute included angle.

49. A bipolar electrosurgical instrument according to claim 42, wherein:
said first blade member has a cutting edge which is defined by an obtuse included angle.

50. A bipolar electrosurgical instrument according to claim 49, wherein:
said first blade member has an electrically non-conductive material on at least part of its shearing surface.

51. A bipolar electrosurgical instrument according to claim 50, wherein:
said electrically non-conductive material of the second blade member is located on substantially all of its shearing surface and said first blade member has an electrically non-conductive material on substantially all of its shearing surface.

52. A bipolar electrosurgical instrument according to claim 42 wherein:

said electrically non-conductive material of the second blade member is located on substantially all of the second blade shearing surface.

53. A bipolar electrosurgical instrument according to claim 42, wherein:

said second blade member further comprises a laminated assembly including a second electrically non-conductive portion.

54. A bipolar electrosurgical instrument according to claim 42, wherein:

said first blade member further comprises a laminated assembly including two electrically non-conductive portions.

\* \* \* \* \*